(12) United States Patent
Tokita et al.

(10) Patent No.: US 10,455,664 B2
(45) Date of Patent: Oct. 22, 2019

(54) ANALYTE-INFORMATION ACQUISITION APPARATUS

(71) Applicant: CANON KABUSHIKI KAISHA, Tokyo (JP)

(72) Inventors: Toshinobu Tokita, Yokohama (JP); Yasuhiro Someda, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/224,379

(22) Filed: Jul. 29, 2016

(65) Prior Publication Data
US 2016/0338178 A1     Nov. 17, 2016

Related U.S. Application Data

(63) Continuation of application No. 14/122,146, filed as application No. PCT/JP2012/062730 on May 11, 2012, now Pat. No. 9,439,267.

(30) Foreign Application Priority Data

May 31, 2011 (JP) .................................. 2011-122741

(51) Int. Cl.
| | |
|---|---|
| *A61B 5/00* | (2006.01) |
| *G01N 29/00* | (2006.01) |
| *G01N 21/35* | (2014.01) |
| *A61B 5/055* | (2006.01) |
| *A61B 8/00* | (2006.01) |
| *G01H 9/00* | (2006.01) |

(Continued)

(52) U.S. Cl.
CPC ....... *H05B 37/0227* (2013.01); *A61B 5/0073* (2013.01); *A61B 5/0095* (2013.01); *A61B 5/489* (2013.01); *A61B 5/6835* (2013.01); *G01J 1/44* (2013.01); *G01N 21/1702* (2013.01); *G01N 29/0672* (2013.01); *G01N 29/14* (2013.01); *H05B 37/02* (2013.01); *A61B 2560/04* (2013.01)

(58) Field of Classification Search
CPC .... H03K 5/1565; H03L 7/0814; G01N 29/00; B60L 11/1811; H02P 6/34; H02P 6/04; H02P 6/08; H02P 27/06; B60K 6/26; A61B 6/00
USPC .......................... 327/149–159; 301/9.1–10.8; 307/9.1–10.8
See application file for complete search history.

(56) References Cited

U.S. PATENT DOCUMENTS

| | | | | |
|---|---|---|---|---|
| 4,830,502 | A * | 5/1989 | Saito | G01N 21/171 356/432 |
| 5,214,282 | A * | 5/1993 | Yamaguchi | B82Y 20/00 250/306 |

(Continued)

FOREIGN PATENT DOCUMENTS

| | | |
|---|---|---|
| JP | 5-228144 A | 9/1993 |
| JP | 9-24034 A | 1/1997 |

(Continued)

*Primary Examiner* — Brandon S Cole
(74) *Attorney, Agent, or Firm* — Canon U.S.A., Inc. I.P. Division

(57) ABSTRACT

To improve the safety of a photoacoustic apparatus by preventing illumination light from being freely emitted. A photoacoustic apparatus includes a position sensor that measures the orientation and/or position of an illumination-light emission end and a control unit that controls light emission from a light source depending on the output of the position sensor.

15 Claims, 8 Drawing Sheets

(51) Int. Cl.
*H05B 37/02* (2006.01)
*G01N 21/17* (2006.01)
*G01N 29/06* (2006.01)
*G01J 1/44* (2006.01)
*G01N 29/14* (2006.01)

(56) References Cited

U.S. PATENT DOCUMENTS

| | | | |
|---|---|---|---|
| 8,649,022 B2* | 2/2014 | Montgomery | A61B 5/0084 356/482 |
| 2007/0206193 A1* | 9/2007 | Pesach | G01N 21/1702 356/432 |
| 2008/0194929 A1* | 8/2008 | Pesach | A61B 5/0066 600/310 |
| 2009/0214440 A1* | 8/2009 | Bohme | A61B 5/055 424/9.37 |
| 2010/0094561 A1* | 4/2010 | Masumura | A61B 5/0073 702/19 |
| 2010/0285518 A1* | 11/2010 | Viator | G01N 21/1702 435/29 |
| 2010/0331662 A1* | 12/2010 | Fukutani | A61B 5/0059 600/407 |
| 2011/0106478 A1* | 5/2011 | Someda | A61B 5/0059 702/104 |
| 2011/0167002 A1* | 7/2011 | Balasubramanian | G06Q 20/04 705/44 |
| 2011/0172513 A1* | 7/2011 | Nakajima | A61B 5/0059 600/407 |
| 2011/0194380 A1* | 8/2011 | Fukutani | A61B 5/0095 367/140 |
| 2011/0245666 A1* | 10/2011 | Den Heeten | A61B 5/0095 600/437 |
| 2012/0150013 A1* | 6/2012 | Peyman | A61B 5/0095 600/407 |
| 2012/0197343 A1* | 8/2012 | Lane | A61B 5/1036 607/49 |
| 2012/0203115 A1* | 8/2012 | Melnik | A61B 5/0059 600/476 |
| 2012/0285248 A1* | 11/2012 | Sudo | A61B 5/0095 73/602 |
| 2013/0031982 A1* | 2/2013 | Sato | A61B 8/08 73/655 |
| 2013/0114859 A1* | 5/2013 | Wanda | A61B 5/0095 382/103 |
| 2013/0331680 A1* | 12/2013 | Furukawa | A61B 5/0095 600/407 |
| 2014/0145648 A1* | 5/2014 | Tokita | A61B 5/0073 315/362 |

FOREIGN PATENT DOCUMENTS

| | | |
|---|---|---|
| JP | 2003-190154 A | 7/2003 |
| JP | 2004-147940 A | 5/2004 |
| JP | 2010-022816 A | 2/2010 |
| JP | 2010-519540 A | 6/2010 |

* cited by examiner

ANALYTE-INFORMATION ACQUISITION APPARATUS

This application is a Continuation of co-pending U.S. patent application Ser. No. 14/122,146 filed Nov. 15, 2013, which is a National Phase Application of International Application PCT/JP2012/062730, filed May 11, 2012, which claims the benefit of Japan Patent Application No. 2011-122741, filed May 31, 2011. The disclosures of U.S. patent application Ser. No. 14/122,146, International Application PCT/JP2012/062730, and Japan Patent Application No. 2011-122741 are hereby incorporated by reference in their entirety.

TECHNICAL FIELD

The present invention relates to an analyte-information acquisition apparatus that emits illumination light to an analyte to image ultrasonic waves released from the analyte.

BACKGROUND ART

Photoacoustic tomography (hereinafter referred to as PAT) is attracting an attention as a method for specifically imaging new blood vessels due to cancer. The PAT is a technology of an imaging system involving irradiating an analyte with illumination light (near-infrared light) and receiving photoacoustic waves generated from the interior of the analyte with an ultrasonic probe. The details of this photoacoustic apparatus are described in NPL 1. However, NPL 1 does not give sufficient consideration to illumination-light irradiation control, in particular, safe irradiation. This sometimes causes the illumination light to irradiate not only the interior of the analyte but also space, and hence there is much room for further improvement in the safety of illumination light irradiation.

On the other hand, a known technology for the safety of irradiation of illumination light, such as laser hair removal, although not the PAT technology, is disclosed in PTL 1. FIGS. 8A and 8B illustrate the configuration of PTL 1. In FIGS. 8A and 8B, an energy releasing surface 101 is a surface that comes into contact with skin, which is to be irradiated with energy, such as light. A support structure 102 holds the energy releasing surface 101 and is accommodated in a housing 104, with contact sensors 103 disposed therebetween. The contact sensors 103 detect contact between the energy releasing surface 101 and skin (not shown) and are disposed so as to surround the energy releasing surface 101. Release of energy is stopped until contact with skin is detected by the contact sensors 103. This allows energy to be emitted only when the energy releasing surface 101 is in fully close contact with skin, thus improving safety in energy irradiation.

However, the related art has the problems below.

In the case of irradiation control using the contact sensors 103, since emission of energy, such as light, is determined depending on whether or not there is contact, the emission has to be stopped depending the object in contact. For example, because energy, such as light, is emitted even if an object other than an object to be irradiated with light is in contact, further improvement has been required. Also when a transparent substance is in contact with energy, such as light, the energy that has passed through the contact object irradiates another object, and thus improvement is needed. Accordingly, control of energy release using the contact sensors 103 is not necessarily perfect, and thus a different safe measure is needed to further improve the safety.

CITATION LIST

Patent Literature

PTL 1 PCT Japanese Translation Patent Publication No. 2006-525036

Non Patent Literature

NPL 1 S. A. Ermilov et al., Development of Laser Optoacoustic and Ultrasonic Imaging System for Breast cancer Utilizing Handheld Array Probes, Photons Plus Ultrasound: Imaging and Sensing 2009, Proc. of SPIE vol. 7177, 2009.

SUMMARY OF INVENTION

The present invention is made in consideration of the foregoing problems.

The present invention enables emission of illumination light to be properly controlled to improve the safety of a photoacoustic apparatus.

Solution to Problem

To solve the above problems, an analyte-information acquisition apparatus according to an aspect of the present invention includes a light emitting unit having an emitting portion that emits light to be applied to an analyte; a probe configured to receive photoacoustic waves that the analyte generates when receiving the light emitted from the light emitting unit and to output an electrical signal; a detecting unit configured to detect the position or the orientation of the emitting portion; and a control unit configured to control the light emitting unit on the basis of a detection result of the detecting unit.

Advantageous Effects of Invention

According to an aspect of the present invention, since illumination light can be prevented from being freely emitted, the safety of an analyte-information acquisition apparatus, such as a photoacoustic apparatus, can be further improved.

DESCRIPTION OF EMBODIMENTS

The present invention is based on the analysis that the risk of directly irradiating an operator or a user and the eyes of a subject, with illumination light can be reduced if illuminating light is emitted at least downwards (in the direction of gravity) with respect to the horizontal direction.

Figure 1:
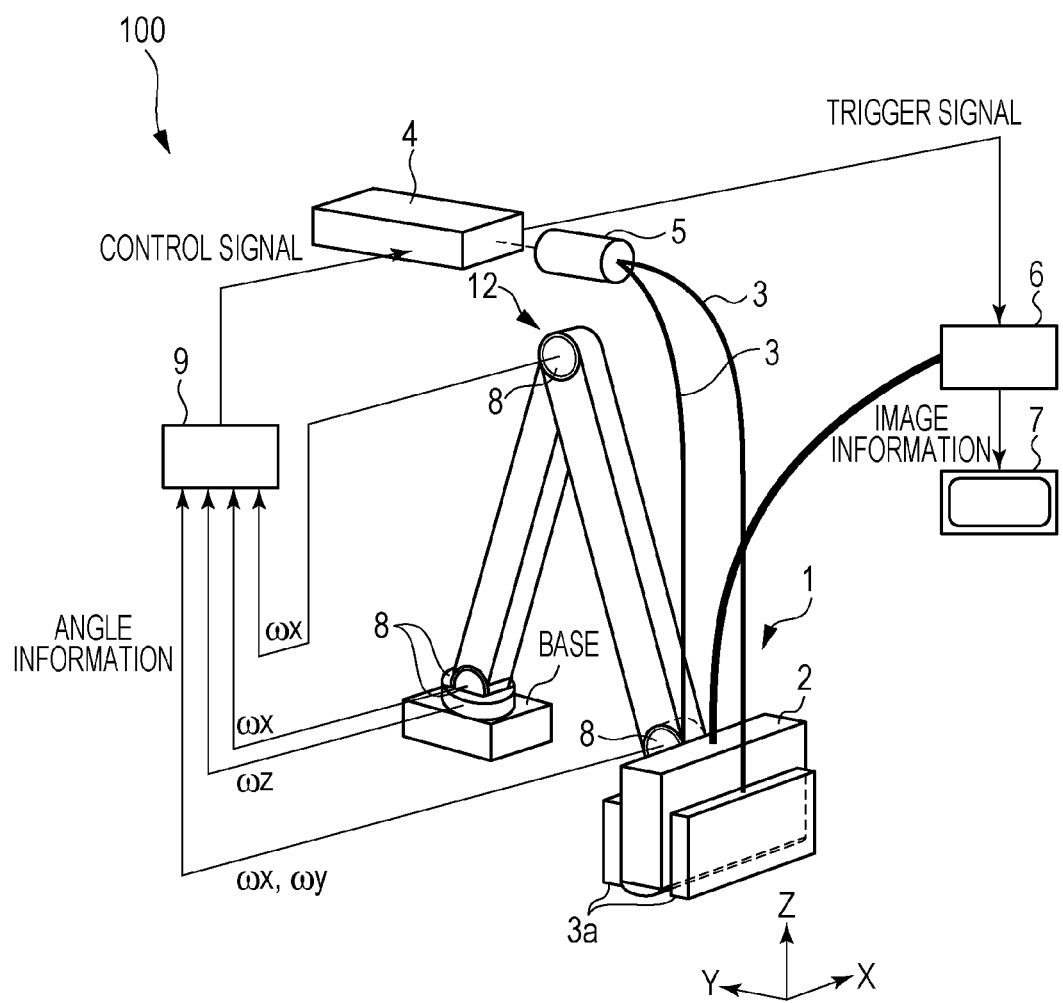
FIG. 1 is a diagram illustrating the configuration of an apparatus according to an embodiment of the present invention.
Figure 2A:
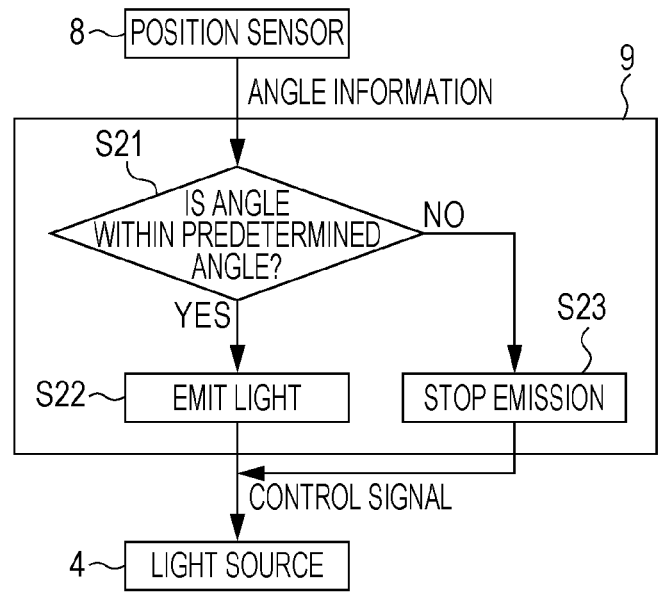
FIG. 2A is a diagram illustrating a control method according to an embodiment of the present invention.
Figure 2B:
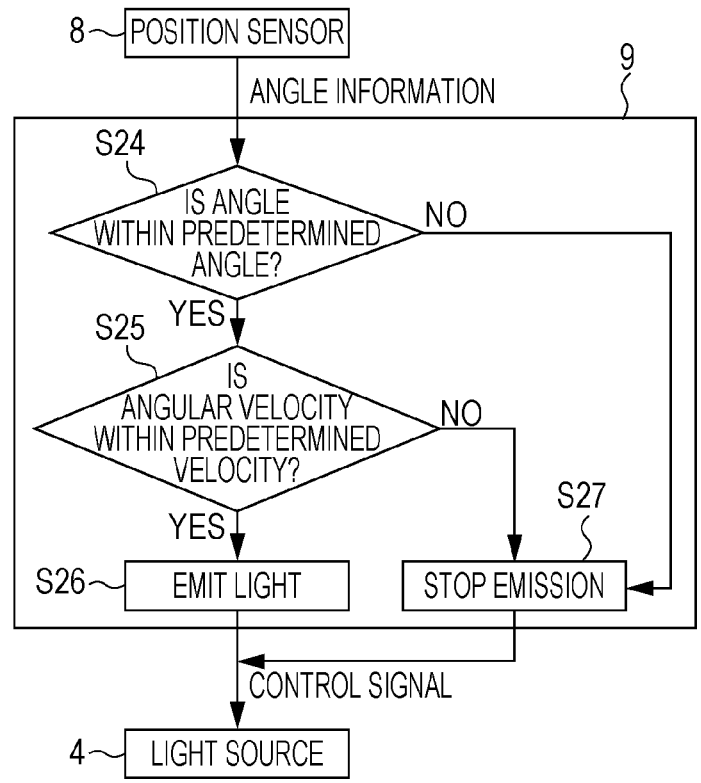
FIG. 2B is a diagram illustrating another control method according to an embodiment of the present invention.

Embodiments of the present invention will be described using the drawings. FIG. 1 is a schematic diagram of a photoacoustic apparatus 100 serving as an analyte-information acquisition apparatus. The photoacoustic apparatus 100 includes a light emitting unit having emitting portions that emit light to be applied to an analyte (not shown), a probe 2 that receives photoacoustic waves that the analyte generates when receiving the light emitted from the light emitting unit and that outputs an electrical signal, position sensors 8 serving as a detecting unit that detects the positions or orientations of the emitting portions, and a control unit 9 that controls the light emitting unit on the basis of detection results of the position sensors 8. The individual components will be described in detail hereinbelow.

The light emitting unit includes a light source 4 that emits illumination light and emission ends 3a serving as emitting portions that emit the light generated from the light source 4 to an analyte (not shown). In the embodiment shown in FIG. 1, since the light from the light source 4 is applied to the analyte through fiber bundles 3, the emitting portions are ends 3a of the fiber bundles 3. However, they are not limited thereto; the light from the light source 4 may be reflected by a mirror or the like and may be directly applied to the analyte. A transparent window may be provided at a portion in contact with or vicinity of the analyte, in which case the transparent window serves as an emitting portion. In FIG. 1, an illumination optical system 5 is interposed between the light source 4 and the emission ends 3a serving as the emitting portions.

The probe 2 may be a transducer array or the like which is constituted by a plurality of devices each constituted by a plurality of oscillators or the like and which converts acoustic waves to an electrical signal. In the description below, the probe 2 and the emission ends 3a are sometimes collectively referred to as a photoacoustic probe 1.

The position sensors 8 detect the positions of the emission ends 3a. In the embodiment shown in FIG. 1, an arm mechanism 12, described later, is provided which serves as a support member that supports the probe 2. The position sensors 8 are disposed at three locations of the arm mechanism 12. An example of the position sensors 8 is an encoder.

The control unit 9 of this embodiment calculates the orientations of the emission ends 3a, that is, the emission direction of the illumination light, on the basis of the angles of the joints of the arm mechanism 12 measured by the encoders of the position sensors 8, described above, and controls the operation of the light emitting unit. Furthermore, the control unit 9 determines the positions and the emitting directions of the emission ends 3a from the length of the arm mechanism 12 and the angles of the joints, which are the detection results of the position sensors 8 (encoders), and controls the operation of the light emitting unit. Examples of a method for controlling the operation of the light emitting unit includes a method of opening and closing an internal shutter of the light source 4 and a method of controlling an internal trigger signal (flash lamp or Q switch). Alternatively, an external shutter may be provided between the light source 4 and the illumination optical system 5, and the open and shut of the shutter may be controlled. The control unit 9 permits and stops generation of light by the light emitting unit on the basis of the detection result of the detecting unit in this way.

This embodiment may include a processing unit 6 and a monitor 7. The processing unit 6 performs various processes, such as amplification, digital conversion, and image reconstruction on the electrical signal that is output on the basis of the photoacoustic waves that the probe 2 receives. The monitor 7 displays image information that the processing unit 6 outputs.

In this embodiment, the positions or orientations of the emission ends 3a of the light emitting unit are detected by the position sensors 8, and the operation of the light emitting unit is controlled by the control unit 9 on the basis of the detection results, as described above. This can prevent erroneous light irradiation when an object other than the analyte is in contact with the light and when a transparent object is in contact with the light, which are problems in light irradiation control using the contact sensors. In addition, with the configuration in which the relative positional relationship among the analyte, the emitting portions of the light emitting unit, and the operator (or the user) during measurement (during the operation of the apparatus) is substantially maintained, as in the analyte-information acquisition apparatus, a malfunction can be prevented with higher accuracy by controlling light emission depending on the positions or orientations of the emitting portions. Specifically, this can reduce the risk of directly irradiating the operator or the user and the eyes of the subject, with illumination light, for example, when illuminating light is directed at least downwards (in the direction of gravity) with respect to the horizontal direction.

Although the foregoing has been described as applied to an example in which an encoder is used as the detecting unit, the detecting unit is not limited thereto; for example, a gyro sensor, an acceleration sensor, a magnetic sensor, an optical sensor, and a camera can be employed. An appropriate combination thereof allows higher-accuracy operation control of the light emitting unit.

Although the foregoing embodiment is configured such that the position sensors 8 are disposed at the arm mechanism 12 serving as a support member that supports the probe 2, the present invention is not limited thereto; the position sensors 8 may be provided at the photoacoustic probe 1, as in the configuration shown in FIG. 6, described later.

Furthermore, an optical system, such as a diffuser, may be provided between the emission ends 3a of the light emitting unit and the analyte.

Examples of the light source 4 include pulse lasers, such as a Nd:YAG laser and an Alexandrite laser. Other examples are a Ti:sa laser and an OPO laser that uses Nd:YAG laser light as exciting light.

The embodiment shown in FIG. 1 is configured such that part of illumination light generated from the light source 4 is split off, and when the output of a photodiode (not shown) measured, serving as a trigger signal, is input, the processing unit 6 causes the probe 2 to acquire a photoacoustic signal. The trigger signal is not limited to the output of the photodiode; it is also possible to use a method of synchronizing the light generated from the light source 4 with a trigger signal input to the processing unit 6.

The arm mechanism 12 serving as a support member that supports the photoacoustic probe 1 has a structure for cancelling the weight of the photoacoustic probe 1 itself. The degree of freedom of the arm mechanism 12 may be a total of six degrees of freedom, that is, X, Y, Z and periaxes (ωx, ωy, ωz). The arm mechanism 12 in the configuration in FIG. 1 is provided with encoders serving as the position sensors 8 at three joints from the photoacoustic probe 1 to the base. The control unit 9 controls the light emitting unit on the basis of information on the outputs of the encoders, the length of the arm mechanism 12, and so on, as described above.

Control methods of the control unit 9 will be described in detail using the flowcharts in FIGS. 2A and 2B and FIGS. 3A and 3B.

Step S21

The control unit 9 acquires angle information using the encoders serving as the position sensors 8. The control unit 9 determines whether the orientations of the emission ends 3a of the fiber bundles 3, which are emission directions of illumination light, are within a predetermined angle.

Step S22

If the determination in S21 is within the predetermined angle, the control unit 9 controls emission from the light source 4 so that light emission is permitted.

Step S23

If the determination in S21 is equal to or larger than the predetermined angle, the control unit 9 controls emission from the light source 4 so that light emission is stopped.

Limiting the emission of illumination light to a predetermined direction can reduce free emission of the illumination light, thus improving the safety. The surfaces of components present in the limited emission direction of the illumination light, facilities, such as a bed, and room environments, such as a floor and walls, are made of materials that scatter and/or absorb the illumination light. For example, for metal, the surface is matted, or plated or coated in dark color, such as black, or flocked paper or cloth is bonded to the surface. This allows illumination light to be scattered or absorbed even if the illumination light irradiates an object other than the analyte, thus further improving the safety. To further ensure the safety, at least the operator or user and the subject should wear laser protection goggles, and a shade curtain should be placed between the eyes of the subject and the photoacoustic probe 1.

Not only the angles of the emission ends 3a of the fiber bundles 3, which are the emission directions of the illuminating light, but also the angular velocities thereof may be objects to be controlled for emission from the light source 4. This will be described using the flowchart in FIG. 2B.

Step S24

The control unit 9 acquires angle information, which is the measured outputs of the encoders. The control unit 9 then determines whether the orientations of the emission ends 3a of the fiber bundles 3 are within a predetermined angle.

Step S25

The control unit 9 obtains the angular velocities of the emission ends 3a of the fiber bundles 3 by time-differentiating the angle information obtained in S24. The control unit 9 then determines whether the angular velocities are within a predetermined velocity. Furthermore, angular acceleration may also be controlled.

Step S26

If both of the determinations in S24 and S25 are within predetermined values, the control unit 9 controls emission from the light source 4 so that light emission is permitted.

Step S27

If either of the determinations in S24 and S25 is equal to or larger than the predetermined value, the control unit 9 controls emission from the light source 4 so that light emission is stopped.

By also detecting the movement of the illumination light in the emission direction in this way, the control unit 9 can control light emission from the light source 4 even if the photoacoustic probe 1 moves suddenly, and hence the safety can be further improved.

A determination value for the illumination light in the emission direction in S21 and S24 is set depending on the analyte. For example, in the case where the analyte is a breast, and a photoacoustic image thereof is acquired with the subject laid on his/her back, the standard emission direction of the illumination light is set at the direction of gravity (−Z direction in FIG. 1). Since the photoacoustic probe 1 is scanned along the analyte to acquire a photoacoustic image, a value within ±90° from the standard direction is set as the determination value. A determination value for the movement of the illumination light in the emission direction (angular velocity) determined in S25 may be set depending on the analyte or the posture of the subject. In the above case, the determination value is set within about ±90°/sec. However, the determination values described here are merely examples and are not limited thereto even if the analyte and the posture of the subject are the same as those described above.

Furthermore, not only the emission direction of the illumination light from the photoacoustic probe 1 but also the position information of the photoacoustic probe 1 can be obtained from the length of the arm mechanism 12 and the outputs of the encoders serving as the position sensors 8. Only when the emission ends 3a of the illumination light are at predetermined positions, the control unit 9 permits the light source 4 to emit light. Next, this control method of the control unit 9 will be described using the flowchart in FIG. 3A.

Step S31

The control unit 9 acquires the position information and the angle information (emission directions) of the emission ends 3a from the outputs of the encoders and the length of the arm mechanism 12. The control unit 9 then determines whether the positions of the emission ends 3a and the emission direction of the illumination light are within a predetermined position and direction.

Step S32

If the determinations in S31 are within the predetermined position and direction, the control unit 9 controls emission from the light source 4 so that light emission is permitted.

Step S33

If the determinations in S31 are equal to or larger than the predetermined position and direction, the control unit 9 controls emission from the light source 4 so that light emission is stopped.

A determination value for the emission position of the illumination light in S31 is set depending on the analyte and the posture of the subject. For example, in the case where the standard emission direction of the illumination light is the direction of gravity (−Z direction in FIG. 1), the position of the photoacoustic probe 1 in the +Z direction is used as a determination value. This allows the emission of the illumination light from the light source 4 to be stopped in a state in which the photoacoustic probe 1 is raised. The determination value in the +Z direction may be set within about 100 mm from an average measuring position to prevent peeping. A determination value in the X-Y direction is set within about ±200 mm from an average measuring position. Of course, the emission direction of the illumination light is also provided with a determination value, as described in S21 and S24 in FIGS. 2A and 2B. By controlling emission from the light source 4 on the basis of not only the emission direction of the illumination light but also the emission position thereof, the safety can be further improved.

Figure 3A:
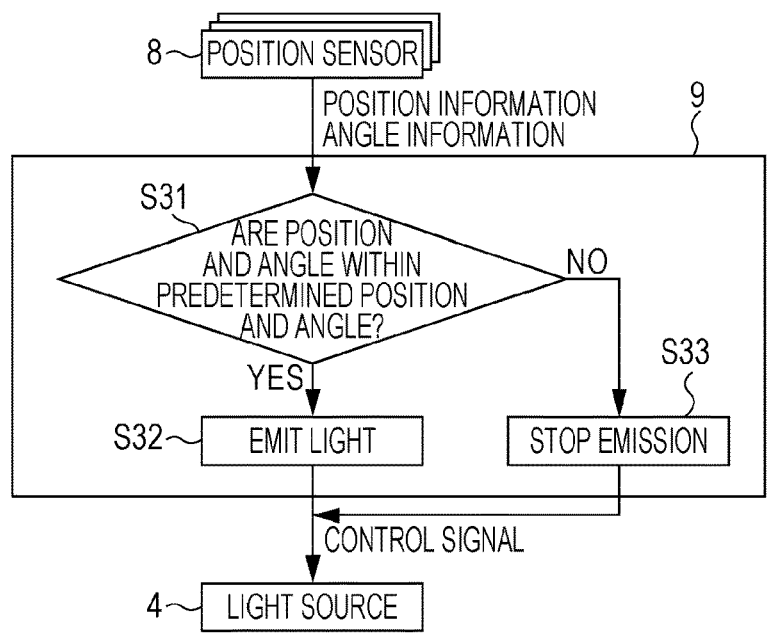
FIG. 3A is a diagram illustrating yet another control method according to an embodiment of the present invention.
Figure 3B:
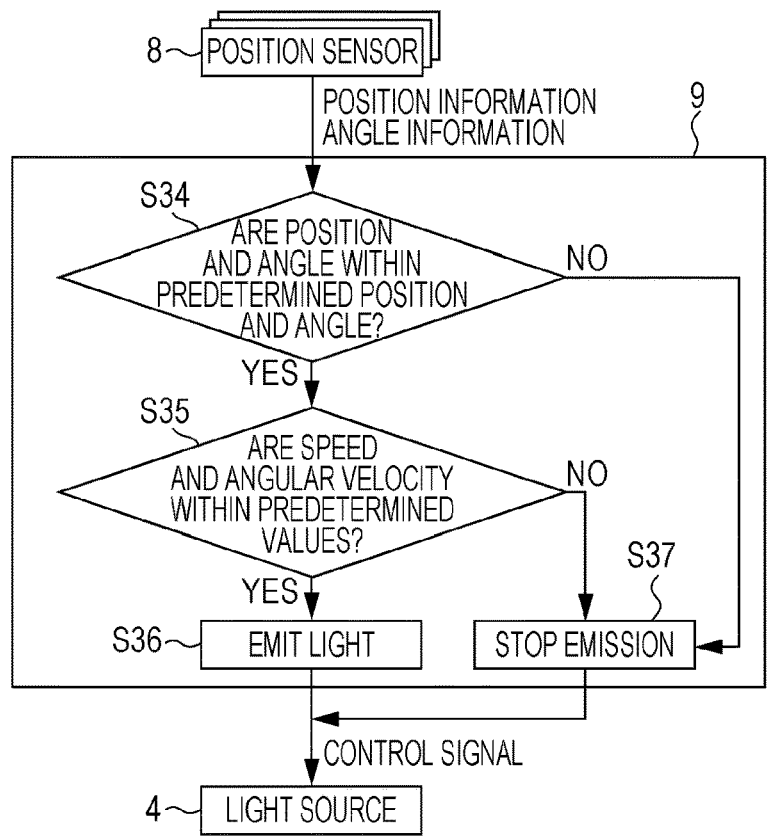
FIG. 3B is a diagram illustrating still another control method according to an embodiment of the present invention.

Furthermore, not only the positions of the emission ends 3a and the emission direction of the illumination light but also the movement thereof may be controlled for emission from the light source 4, as in FIG. 3B.

Step S34

The control unit 9 acquires the position information and the angle information (emission directions) of the emission ends 3a from the outputs of the encoders serving as the position sensors 8 and the length of the arm mechanism 12. The control unit 9 then determines whether the positions of the emission ends 3a and the emission direction of the illumination light are within a predetermined position and direction.

Step S35

The control unit 9 obtains the velocities and the angular velocities of the emission ends 3a by time-differentiating the position information and the angle information of the emission ends 3a obtained in S34. The control unit 9 then determines whether the velocities and the angular velocities are within predetermined velocities and angular velocities. Furthermore, acceleration and angular acceleration may also be controlled.

Step S36

If both of the determinations in S34 and S35 are within predetermined values, the control unit 9 controls emission from the light source 4 so that light emission is permitted.

Step S37

If either of the determinations in S34 and S35 is equal to or lager than the predetermined value, the control unit 9 controls emission from the light source 4 so that light emission is stopped.

Reference determination values for the movement of the illumination-light emission ends 3a are set to at most, for example, a velocity of 200 mm/sec. and a gravity acceleration. By also limiting the movement of the emission ends 3a, the control unit 9 can control light emission from the light source 4 even if the photoacoustic probe 1 moves suddenly, and hence the safety can be further improved.

The present invention will be described in more detail using examples.

EXAMPLE 1

In this example, a PAT image was acquired by the photoacoustic apparatus described in FIG. 1. A Nd:YAG laser and a Ti:sa laser using Nd:YAG laser light as exciting light were used as the light source 4. The fiber bundles 3 were used to propagate the illumination light. The emission ends 3a of the fiber bundles 3 were each provided with an enlarging optical system and a diffuser. The photoacoustic probe 1 integrally accommodates the probe 2, the emission ends 3a of the fiber bundles, the enlarging optical systems, and the diffusers. The emission direction of the illumination light was aligned with a direction in which the photoacoustic probe 1 acquires a photoacoustic signal. The photoacoustic probe 1 was mounted on the arm mechanism 12, whose degrees of freedom were set to a total of six degrees of freedom, that is, X, Y, Z and periaxes ($\omega x$, $\omega y$, $\omega z$). The arm mechanism 12 is provided with encoders serving as the position sensors 8 at joints from the photoacoustic probe 1 to the base. The encoders measure the angles of the joints. The control unit 9 can calculate the direction of the photoacoustic probe 1, specifically, the orientations of the emission ends 3a and hence the emission direction of the illumination light by summing up the outputs of the encoders for each of rotation components. Furthermore, the control unit 9 can obtain the positions and emission directions of the illumination-light emission ends 3a from the lengths of the arms of the arm mechanism 12 and the outputs of the encoders serving as the position sensors 8, that is, the angles of the joints. Here, all of the arm lengths were set to about 500 mm to provide a sufficient movable region of the photoacoustic probe 1.

Figure 4:
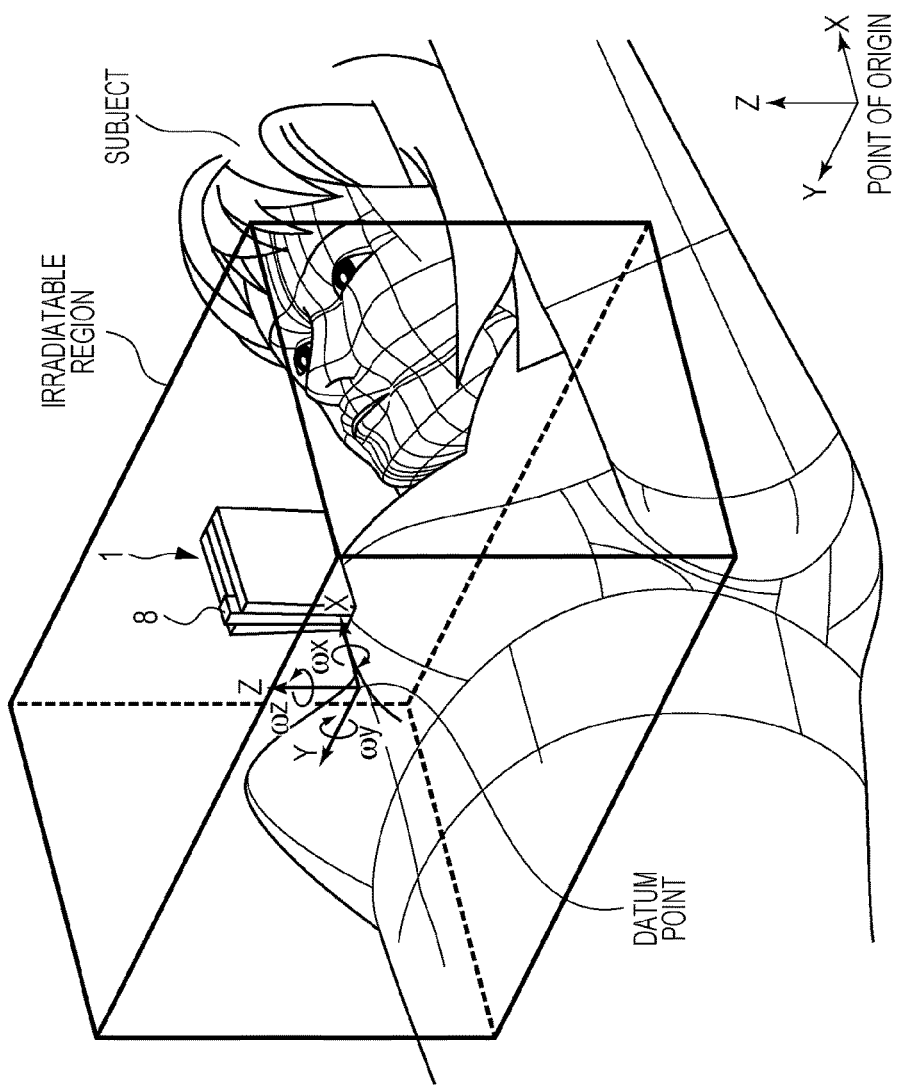
FIG. 4 is a diagram illustrating an illumination-light irradiation region in Example 1 of the present invention.

For the emission control of the light source 4, the control method described in the flowchart of FIG. 3B was applied, and light emission and stopping thereof were controlled using a shutter built in the Nd:YAG laser. Next, determination values for the emission direction and emission position of the illumination light will be described using FIG. 4.

The center of the breast of the subject was set as the datum point of the apparatus, and the subject was laid on his/her back, with the breast located thereat. A region in the range of $-150$ mm$<$X$<+200$ mm, $-200$ mm$<$Y$<+200$ mm, and $-50$ mm$<$Z$<+50$ mm from the datum point was set to an irradiatable region. In the range of X$\geq$0, the range of $0<\omega y<+90°$ was set to an irradiatable region. In the range of X$<$0, a region within the range of $-50$ mm$<$Z$<+10$ mm and $-90°<\omega y<0$ was set to an irradiatable region. In other ranges, a region within $-90°<\omega x<+90°$ and $-90°<\omega y<+90°$ was set to an irradiation region. The velocities on the individual axes were set to 200 mm/sec. or lower, the accelerations were set at equal to or lower than the gravitational acceleration, and the angular velocities were set to $+/-90°$/sec. or lower as determination values (irradiatable).

The above configuration prevented the operator or user and the eyes of the subject from being directly irradiated with the illumination light, thus improving the safety.

EXAMPLE 2

Figure 5:
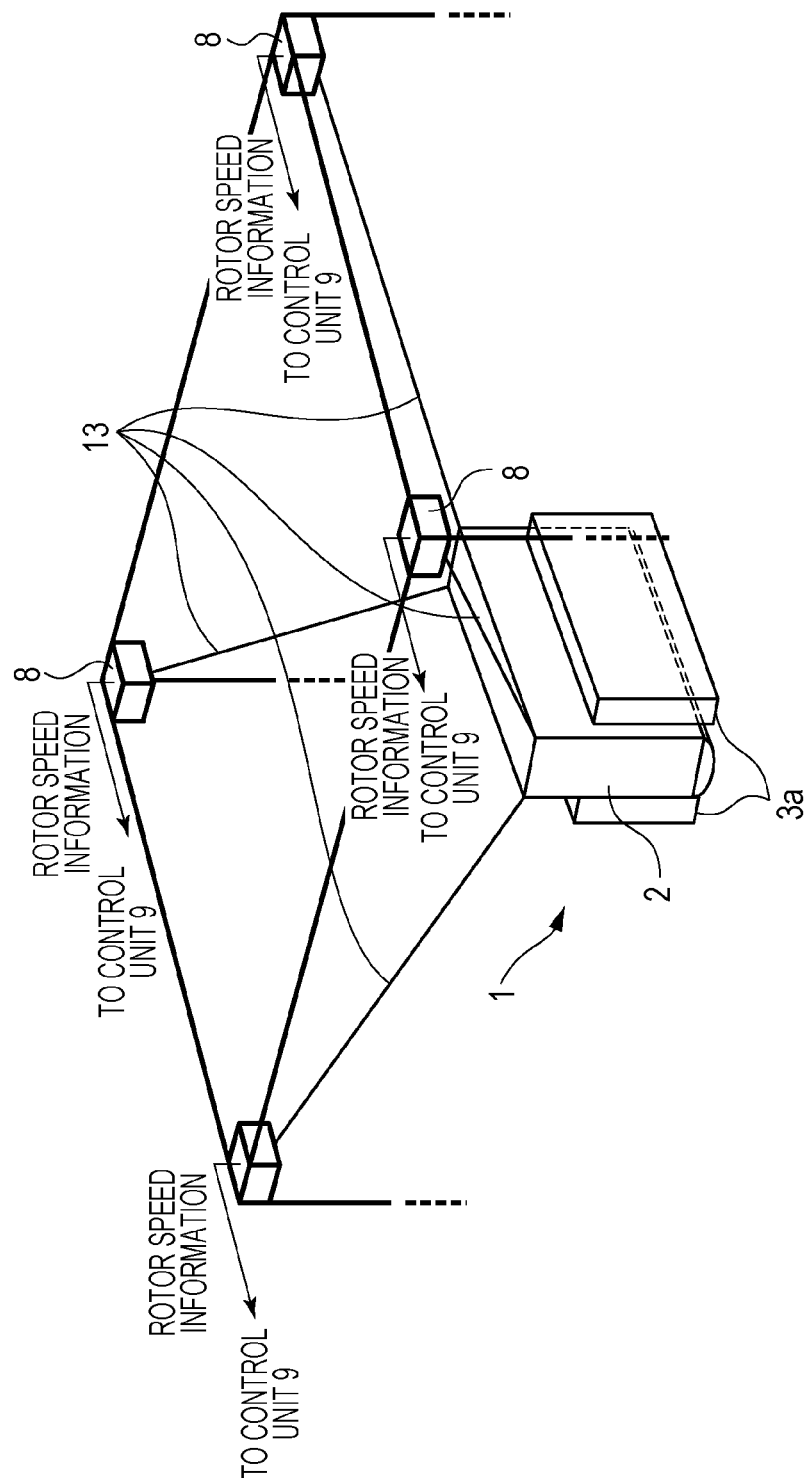
FIG. 5 is a diagram illustrating a support member in Example 2 of the present invention.

Example 2 describes a support member for the photoacoustic probe 1 different from that in Example 1. In Example 2, the photoacoustic probe 1 is supported by connecting the photoacoustic probe 1 to the position sensors 8 (encoders) with wires 13, as in FIG. 5. The individual encoders accommodate rotors for the wires 13 and measure the position of the photoacoustic probe 1 from the rotational speeds of the rotors. In this case, however, if the wires 13 loosen, the measurement accuracy of the position of the photoacoustic probe 1 decreases. Therefore, a winding mechanism or a motor driving mechanism is applied to the rotors to prevent the wires 13 from loosening. In Example 2, sensors (load cells) (not shown) for measuring the tension of the wires 13 and motors for winding the wires 13 were provided at the rotors, and feedback control was performed so as to maintain the tension.

Also in Example 2, light emission is controlled according to the flowchart in FIG. 3B, as in Example 1. The datum point of the apparatus and the irradiatable region of the illumination light were set to be similar to Example 1.

The above configuration allows the positions and orientations of the emission ends 3a to be measured even if the photoacoustic probe 1 is mounted on a support member other than the arm mechanism 12. Controlling the emission of the illumination light prevented the operator or user and the eyes of the subject from being directly irradiated with the illumination light, thus improving the safety.

EXAMPLE 3

In Example 1 and Example 2, the photoacoustic probe 1 is mounted on a support member. In Example 3, the photoacoustic probe 1 is not mounted on a support member, but the photoacoustic probe 1 is provided with the position sensors 8 to measure the orientations of the emission ends 3*a*.

Figure 6:
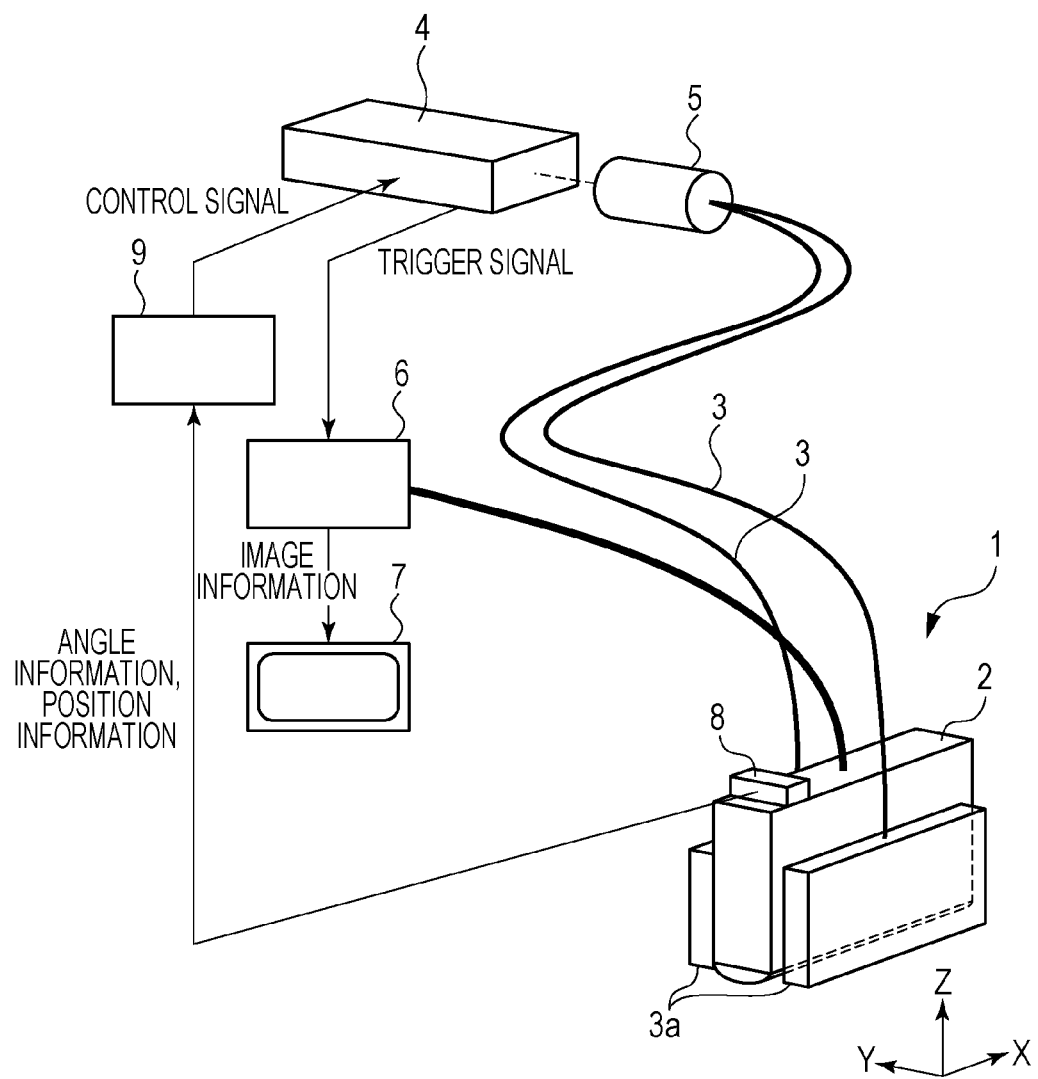
FIG. 6 is a diagram illustrating an apparatus configuration having no support member in Example 3 of the present invention.

Also in FIG. 6, since the same components as those in the other drawings described above are denoted by the same reference signs, descriptions thereof will be omitted. In FIG. 6, a gyro sensor (vibrating structure gyroscope) is applied to the position sensor 8. The measurement axes of the gyro sensor are the X-axis (ωx) and the Y-axis (ωy). The output of the gyro sensor is an angular velocity. The angles of the emission ends 3*a* of the fiber bundles 3 were obtained by calibrating the gyro sensor, with the emission ends 3*a* of the illumination light placed in the horizontal position, and by integrating the output. The control method described in the flowchart of FIG. 2B was applied to control the emission. A determination was made, with the irradiatable angle set to the range of −90°<ωx<+90° and −90°<ωy<0, and the irradiatable angular velocity set to the range of ±90°/sec. or lower.

The above configuration allows the emission to be stopped at least when the emission ends 3*a* are directed upwards even if the photoacoustic probe 1 is not mounted on a support member. This could improve the safety without the illumination light being freely emitted into the space.

EXAMPLE 4

Although the position sensor 8 of Example 3 is a gyro sensor, Example 4 is further provided with an acceleration sensor. The gyro sensor outputs a measurement result (detection result) depending on the angular velocity, and the acceleration sensor outputs a measurement result depending on the acceleration. The measurement axes of the gyro sensor in FIG. 6 were three axes, that is, the X-axis (ωx), the Y-axis (ωy), and the Z-axis (ωz). The measurement axes of the acceleration sensor were three axes, that is, X, Y, and Z-axes. The outputs of the gyro sensor and the acceleration sensor need to be integrated to determine the positions and the velocities of the movement of the emission ends 3*a*. Position information obtained by integrating the output of the position sensor 8 is a position relative to that at the start of measurement. Accordingly, the position sensor 8 needs to be calibrated in advance, with the photoacoustic probe 1 located at the point of origin. Thus, Example 4 is configured such that the photoacoustic probe 1 is disposed at the point of origin provided in advance, and in this state, the gyro sensor and the acceleration sensor were calibrated. The datum point of the apparatus was managed using a distance from the calibrated point of origin. This allows the position and angle of the photoacoustic probe 1 in the spatial coordinates of X, Y, Z, ωx, and ωy to be obtained.

The subject was laid on his/her back so that the center of the breast thereof is located at the datum point. The datum point and the illumination-light irradiatable region were set to be the same as those of Example 1, and the control method described in the flowchart of FIG. 3B was applied to control emission from the light source 4.

Figure 7:
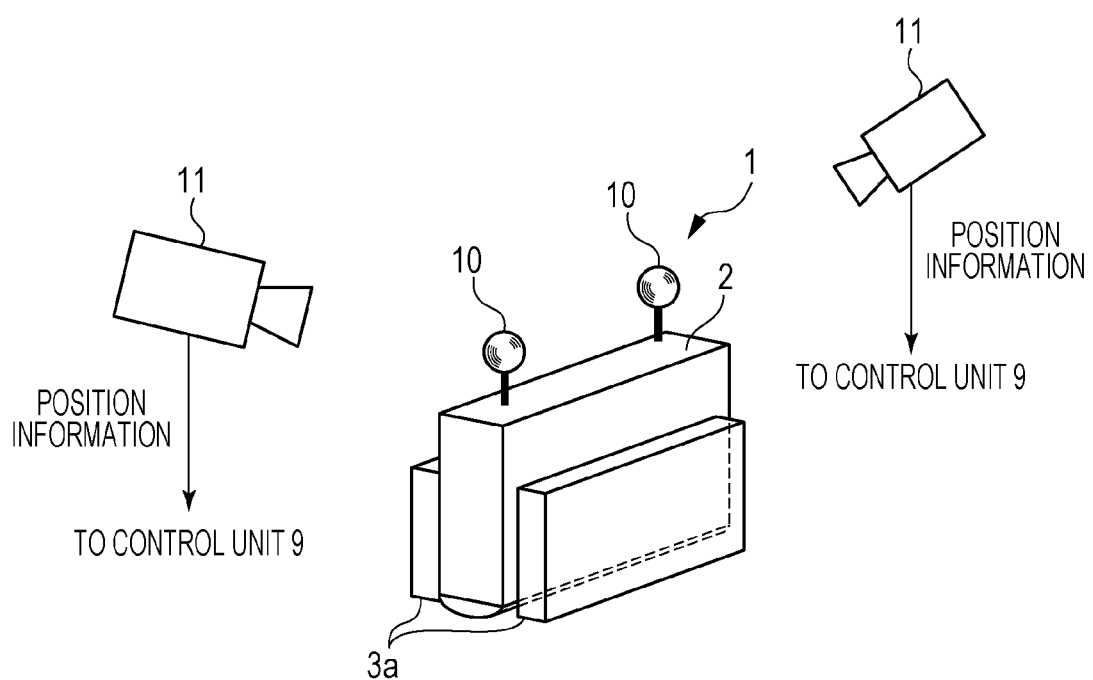
FIG. 7 is a diagram illustrating another position sensor in Example 4 of the present invention.
Figure 8A:
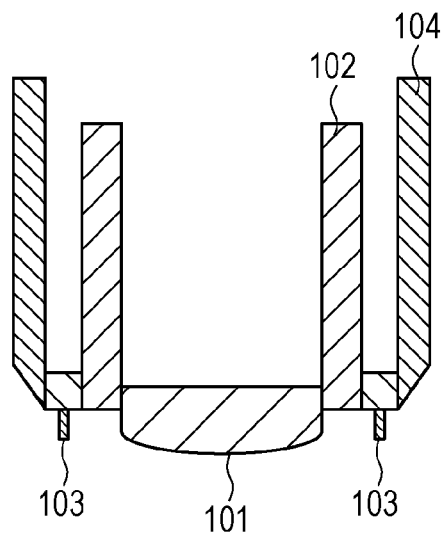
FIG. 8A is a cross-sectional view of a photoacoustic apparatus of a background art.
Figure 8B:
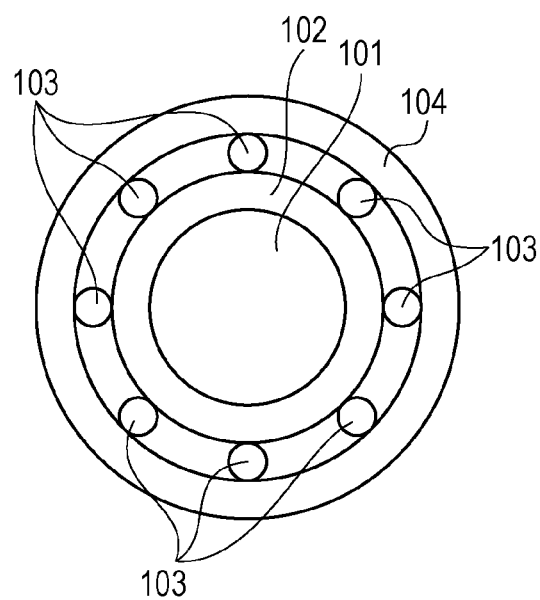
FIG. 8B is a bottom view of the photoacoustic apparatus in FIG. 8A.

The position sensor 8 that detects the angle and position of the photoacoustic probe 1 can be substituted by another sensor other than those described above. For example, as shown in FIG. 7, a method of controlling emission from the light source 4 with the control unit 9 is also possible, in which markers 10 are mounted on the photoacoustic probe 1, and the positions of the markers 10 are detected using a plurality of cameras 11 disposed in a space. Other examples of the position sensor 8 include a magnetic sensor and an optical sensor.

The above configuration allowed the position and orientation of the illumination-light emission ends 3*a* to be measured without the need for mounting the photoacoustic probe 1 on a support member and prevented the operator or user and the eyes of the subject from being directly irradiated with the illumination light, thus improving the safety.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An information acquisition apparatus comprising:
    a light emitting unit including an emitting portion from which light is emitted;
    a probe configured to receive a photoacoustic wave generated in an object in response to an irradiation of the light onto the object and to output an electrical signal;
    a detecting unit configured to detect a direction in which the light is to be emitted from the emitting portion; and
    a control unit configured to control emission of the light on a basis of at least the detected direction of the light to be emitted from the emitting portion,
    wherein the control unit controls the light emitting unit in such a manner that the emitting portion does not emit light in a case where it is determined that the detected direction is not within a predetermined value, on the basis of the detection result of the detecting unit.

2. The information acquisition apparatus according to claim 1, wherein the detecting unit is any of an encoder, a gyro sensor, an acceleration sensor, a magnetic sensor, an optical sensor, and a camera.

3. The information acquisition apparatus according to claim 1, wherein the control unit controls the light emitting unit in such a manner that the emitting portion emits light in a case where it is determined that the detected direction is within a predetermined value, on the basis of the detection result of the detecting unit.

4. The information acquisition apparatus according to claim 3, wherein the control unit controls the light emitting unit in such a manner that the emitting portion does not emit light in a case where it is determined that the detected direction is directed downwards with respect to a horizontal direction.

5. The information acquisition apparatus according to claim 1, wherein the detecting unit is disposed on a support member supporting the probe.

6. The information acquisition apparatus according to claim 1, wherein the detecting unit is disposed on the probe.

7. The information acquisition apparatus according to claim 1, wherein the emitting portion is an end portion of an optic fiber.

8. The information acquisition apparatus according to claim 7, wherein the control unit acquires angle information concerning the direction.

9. The information acquisition apparatus according to claim 8, wherein the control unit determines whether the direction is within a predetermined angle.

10. The information acquisition apparatus according to claim 9, wherein the control unit determines the orientation of the probe with respect to a direction of gravity.

11. The information acquisition apparatus according to claim 1, wherein the light emitting unit is integrated with the probe.

12. The information acquisition apparatus according to claim 1, wherein the object is an analyte.

13. A controller of an acoustic wave reception apparatus comprising:
   a light emitting unit from which light is emitted; and
   a transducer that outputs a reception signal in response to a reception of an acoustic wave,
   wherein the controller is configured to control the light emitting unit in such a manner that the light emitting unit does not emit light in a case where a direction in which the light is to be emitted from the light emitting unit is not within a predetermined value.

14. The controller according to claim 13, wherein the controller allows emission of the light in a case where the direction is within the predetermined value, and wherein the predetermined value is angles below a horizontal direction.

15. The controller according to claim 13, wherein the predetermined value is angles above a horizontal direction.

\* \* \* \* \*